(12) United States Patent
Bramucci et al.

(10) Patent No.: US 8,017,364 B2
(45) Date of Patent: Sep. 13, 2011

(54) SOLVENT TOLERANT MICROORGANISMS

(75) Inventors: Michael G. Bramucci, Boothwyn, PA (US); Helene M. A. Kane, Woodbury, NJ (US); Vasantha Nagarajan, Wilmington, DE (US)

(73) Assignee: Butamax(TM) Advanced Biofuels LLC

( * ) Notice: Subject to any disclaimer, the term of this patent is extended or adjusted under 35 U.S.C. 154(b) by 463 days.

(21) Appl. No.: 11/949,793

(22) Filed: Dec. 4, 2007

(65) Prior Publication Data

US 2008/0138870 A1 Jun. 12, 2008

Related U.S. Application Data

(60) Provisional application No. 60/869,599, filed on Dec. 12, 2006.

(51) Int. Cl.
*C12P 7/16* (2006.01)
*C12P 1/20* (2006.01)

(52) U.S. Cl. ..................... 435/160; 435/252.9

(58) Field of Classification Search .................. None
See application file for complete search history.

(56) References Cited

U.S. PATENT DOCUMENTS

| | | | |
|---|---|---|---|
| 5,192,673 | A | 3/1993 | Jain et al. |
| 6,358,717 | B1 | 3/2002 | Blaschek et al. |
| 6,960,465 | B1 | 11/2005 | Papoutsakis et al. |
| 2007/0218533 | A1 | 9/2007 | Gill et al. |
| 2007/0259410 | A1 | 11/2007 | Donaldson et al. |
| 2007/0292927 | A1* | 12/2007 | Donaldson et al. ........... 435/160 |

FOREIGN PATENT DOCUMENTS

WO    WO 2007/130518 A2    11/2007

OTHER PUBLICATIONS

U.S. Appl. No. 11/527,995, filed Sep. 27, 2006, Gail K. Donaldson et al.
U.S. Appl. No. 60/796,816, filed May 2, 2006, Gail K. Donaldson et al.
U.S. Appl. No. 11/586,315, filed Oct. 25, 2006, Gail K. Donaldson et al.
D. R. Woods, The Genetic Engineering of Microbiol Solvent Production, Trends in Biotechnology, 1995, vol. 13:259-264.
M. Matsumoto et al., Toxicity of Ionic Liquids and Organic Solvents to Lactic Acid-Producing Bacteria, Journal of Bioscience and Bioengineering, 2004, vol. 98:344-347.
Ullmann's Encyclopedia of Industrial Chemistry, Butanols, $6^{th}$ Edition, 2003, vol. 5:716-719.
Carlini et al., Guerbet Condensation of Methanol With N-Propanol to Isobutyl Alcohol Over Hetergeneous Copper Chromite/Mg-Al1 Mixed Oxides Catalysts, J. Molec. Catal., A:Chem., 2004, vol. 220:215-220.
Girbal et al., Regulation of Solvent Production in Clostridium Acetobutylicum, Trends in Biotechnology, 1998, vol. 16:11-16.
Tomas et al., Overexpression of groESL in Clostridium Acetobutylicum Results in Increased Solvent Production and Tolerance, Prolonged Metabolism, and Changes in the Cell'S Transcriptional Program, Appl. Environ. Microbiol., 2003, vol. 69:4951-4965.
Quratulain et al., Development and Characterization of Butanol-Resistant Strain of Clostridium Acetobutylicum in Molasses Medium, Folia Microbiologica, 1995, vol. 40:467-471.
Soucaille et al. Butanol Tolerance and Autobacteriocin Production by Clostridium Acetobutylicum, Current Microbiology, 1987, vol. 14:295-299.
Desmond et al., Improved Stress Tolerance of GroESL-Overproducing *Lactococcus lactis* and Probiotic *Lactobacillus paracasei* NFBC 338, Appl. Environ. Microbiol., 2004, vol. 70:5929-5936.
Sardessai et al., Organic Solvent-Tolerant Bacteria in Mangrove Ecosystem, Current Science, 2002, vol. 82:622-623.
Bieszkiewicz et al., Studies on the Resistance of Activated Sludge Bacteria to High Concentrations of Methanol, Butanol, Glycol Cyclohexanone and Cyclohexylamine, Acta Microbiologica Polonica, 1987, vol. 36:259-265.
Couto et al. Enhancement of Apparent Resistance to Ethanol in *Lactobacillus hilgardii*, Biotechnol. Lett., 1997, vol. 19:487-490.
Ingram et al., Effects of Alcohols on Micro-Organisms, Adv. Microbial. Physiol., 1984, vol. 25:253-300.
International Preliminary Report on Patentability of Corresponding International Application No. PCT/US2007/025292, Dated Jun. 16, 2009.
Nternational Search Report of Corresponding International Application No. PCT/US2007/025292, Dated May 6, 2008.

* cited by examiner

*Primary Examiner* — Herbert J. Lilling

(57) ABSTRACT

*Pediococcus* bacteria having enhanced tolerance to butanols have been isolated. The bacteria are useful for the fermentative production of butanol.

5 Claims, 2 Drawing Sheets

SEQUENCE LISTING

<160> NUMBER OF SEQ ID NOS: 44

<210> SEQ ID NO 1
<211> LENGTH: 1179
<212> TYPE: DNA
<213> ORGANISM: Clostridium acetobutylicum

<400> SEQUENCE: 1

```
atgaaagaag ttgtaatagc tagtgcagta agaacagcga ttggatctta tggaaagtct      60
cttaaggatg taccagcagt agatttagga gctacagcta taaggaagc agttaaaaaa     120
gcaggaataa aaccagagga tgttaatgaa gtcattttag gaaatgttct tcaagcaggt     180
ttaggacaga atccagcaag acaggcatct tttaaagcag gattaccagt tgaaattcca     240
gctatgacta ttaataaggt ttgtggttca ggacttagaa cagttagctt agcagcacaa     300
attataaaag caggagatgc tgacgtaata atagcaggtg gtatggaaaa tatgtctaga     360
gctccttact tagcgaataa cgctagatgg ggatatagaa tgggaaacgc taaatttgtt     420
gatgaaatga tcactgacgg attgtgggat gcatttaatg attaccacat gggaataaca     480
gcagaaaaca tagctgagag atggaacatt tcaagagaag aacaagatga gtttgctctt     540
gcatcacaaa aaaagctga agaagctata aaatcaggtc aatttaaaga tgaaatagtt     600
cctgtagtaa ttaaaggcag aaagggagaa actgtagttg atacagatga gcaccctaga     660
tttggatcaa ctatagaagg acttgcaaaa ttaaaacctg ccttcaaaaa agatggaaca     720
gttacagctg gtaatgcatc aggattaaat gactgtgcag cagtacttgt aatcatgagt     780
gcagaaaaag ctaaagagct tggagtaaaa ccacttgcta gatagtttc ttatggttca     840
gcaggagttg acccagcaat aatgggatat ggaccttct atgcaacaaa agcagctatt     900
gaaaaagcag ttggacagt tgatgaatta gatttaatag aatcaaatga agcttttgca     960
gctcaaagtt tagcagtagc aaaagattta aaatttgata tgaataaagt aaatgtaaat    1020
ggaggagcta ttgcccttgg tcatccaatt ggagcatcag gtgcaagaat actcgttact    1080
cttgtacacg caatgcaaaa aagagatgca aaaaaggct agcaacttt atgtataggt    1140
ggcggacaag gaacagcaat attgctagaa aagtgctag                          1179
```

<210> SEQ ID NO 2
<211> LENGTH: 392
<212> TYPE: PRT
<213> ORGANISM: Clostridium acetobutylicum

<400> SEQUENCE: 2

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110
```

-continued

```
Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Gln Asp
            165                 170                 175

Glu Phe Ala Leu Ala Ser Gln Lys Lys Ala Glu Ala Ile Lys Ser
                180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca      60
ttaaaggatg tacctgcaac agagttagga gctatagtaa taaggaagc tgtaagaaga     120 gctaatataa atccaaatga gattaatgaa gttattttg gaaatgtact tcaagctgga     180
ttaggccaaa acccagcaag acaagcagca gtaaaagcag gattaccttt agaaacacct     240
gcgtttacaa tcaataaggt ttgtggttca ggtttaagat ctataagttt agcagctcaa     300
attataaaag ctggagatgc tgataccatt gtagtaggtg gtatggaaaa tatgtctaga     360
tcaccatatt tgattaacaa tcagagatgg ggtcaaagaa tgggagatag tgaattagtt     420
gatgaaatga taaaggatgg tttgtgggat gcatttaatg atatcatat gggagtaact     480 gcagaaaata ttgcagaaca atggaatata acaagagaag agcaagatga attttcactt     540
```

```
atgtcacaac aaaaagctga aaaagccatt aaaaatggag aatttaagga tgaaatagtt      600
cctgtattaa taaagactaa aaaaggtgaa atagtctttg atcaagatga atttcctaga      660
ttcggaaaca ctattgaagc attaagaaaa cttaaaccta ttttcaagga aaatggtact      720
gttacagcag gtaatgcatc cggattaaat gatggagctg cagcactagt aataatgagc      780
gctgataaag ctaacgctct cggaataaaa ccacttgcta agattacttc ttacggatca      840
tatggggtag atccatcaat aatgggatat ggagcttttt atgcaactaa agctgcctta      900
gataaaatta atttaaaacc tgaagactta gatttaattg aagctaacga ggcatatgct      960
tctcaaagta tagcagtaac tagagattta aatttagata tgagtaaagt taatgttaat     1020
ggtggagcta tagcacttgg acatccaata ggtgcatctg gtgcacgtat tttagtaaca     1080
ttactatacg ctatgcaaaa aagagattca aaaaaaggtc ttgctactct atgtattggt     1140
ggaggtcagg gaacagctct cgtagttgaa agagactaa                            1179
```

<210> SEQ ID NO 4
<211> LENGTH: 392
<212> TYPE: PRT
<213> ORGANISM: Clostridium acetobutylicum

<400> SEQUENCE: 4

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
                20                  25                  30

Val Ile Lys Glu Ala Val Arg Arg Ala Asn Ile Asn Pro Asn Glu Ile
            35                  40                  45

Asn Glu Val Ile Phe Gly Asn Val Leu Gln Ala Gly Leu Gly Gln Asn
        50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270
```

```
Ala Lys Ile Thr Ser Tyr Gly Ser Tyr Gly Val Asp Pro Ser Ile Met
        275                 280                 285
Gly Tyr Gly Ala Phe Tyr Ala Thr Lys Ala Ala Leu Asp Lys Ile Asn
    290                 295                 300
Leu Lys Pro Glu Asp Leu Asp Leu Ile Glu Ala Asn Glu Ala Tyr Ala
305                 310                 315                 320
Ser Gln Ser Ile Ala Val Thr Arg Asp Leu Asn Leu Asp Met Ser Lys
                325                 330                 335
Val Asn Val Asn Gly Gly Ala Ile Ala Leu Gly His Pro Ile Gly Ala
                340                 345                 350
Ser Gly Ala Arg Ile Leu Val Thr Leu Leu Tyr Ala Met Gln Lys Arg
            355                 360                 365
Asp Ser Lys Lys Gly Leu Ala Thr Leu Cys Ile Gly Gly Gly Gln Gly
    370                 375                 380
Thr Ala Leu Val Val Glu Arg Asp
385                 390
```

<210> SEQ ID NO 5
<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt      60
gcagctaaag gatttgaagt agtattaaga gatattaaag atgaatttgt tgatagagga    120
ttagatttta tcaataaaaa tctttctaaa ttagttaaaa aaggaaagat agaagaagct    180
actaaagttg aaatcttaac tagaattttc cggaacagtt gaccttaatat ggcagctgat    240
tgcgatttag ttatagaagc agctgttgaa agaatggata ttaaaaagca gatttttgct    300
gacttagaca atatatgcaa gccagaaaca attcttgcat caaatacatc atcactttca    360
ataacagaag tggcatcagc aactaaaaga cctgataagg ttataggtat gcatttcttt    420
aatccagctc ctgttatgaa gcttgtagag gtaataagag aatagctac atcacaagaa    480
acttttgatg cagttaaaga gacatctata gcaataggaa aagatcctgt agaagtagca    540
gaagcaccag gatttgttgt aaatagaata ttaataccaa tgattaatga agcagttggt    600
atattagcag aaggaatagc ttcagtagaa gacatagata agctatgaa acttggagct    660
aatcacccaa tgggaccatt agaattaggt gattttatag tcttgatat atgtcttgct    720
ataatggatg ttttatactc agaaactgga gattctaagt atagaccaca tacattactt    780
aagaagtatg taagagcagg atggcttgga agaaaatcag gaaaaggttt ctacgattat    840
tcaaaataa                                                             849
```

<210> SEQ ID NO 6
<211> LENGTH: 282
<212> TYPE: PRT
<213> ORGANISM: Clostridium acetobutylicum

<400> SEQUENCE: 6

```
Met Lys Lys Val Cys Val Ile Gly Ala Gly Thr Met Gly Ser Gly Ile
1               5                  10                  15
Ala Gln Ala Phe Ala Ala Lys Gly Phe Glu Val Val Leu Arg Asp Ile
            20                  25                  30
Lys Asp Glu Phe Val Asp Arg Gly Leu Asp Phe Ile Asn Lys Asn Leu
        35                  40                  45
```

```
Ser Lys Leu Val Lys Gly Lys Ile Glu Glu Ala Thr Lys Val Glu
    50              55                  60

Ile Leu Thr Arg Ile Ser Gly Thr Val Asp Leu Asn Met Ala Ala Asp
65                  70                  75                  80

Cys Asp Leu Val Ile Glu Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
            115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
                180                 185                 190

Pro Met Ile Asn Glu Ala Val Gly Ile Leu Ala Glu Gly Ile Ala Ser
                195                 200                 205

Val Glu Asp Ile Asp Lys Ala Met Lys Leu Gly Ala Asn His Pro Met
210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
                260                 265                 270

Ser Gly Lys Gly Phe Tyr Asp Tyr Ser Lys
        275                 280

<210> SEQ ID NO 7
<211> LENGTH: 786
<212> TYPE: DNA
<213> ORGANISM: Clostridium acetobutylicum

<400> SEQUENCE: 7
atggaactaa acaatgtcat ccttgaaaag gaaggtaaag ttgctgtagt taccattaac      60
agacctaaag cattaaatgc gttaaatagt gatacactaa agaaatggat ttatgttata    120
ggtgaaattg aaaatgatag cgaagtactt gcagtaattt taactggagc aggagaaaaa    180
tcatttgtag caggagcaga tatttctgag atgaaggaaa tgaataccat gaaggtaga     240 aaattcggga tacttggaaa taaagtgttt agaagattag aacttcttga aaagcctgta    300
atagcagctg ttaatggttt tgctttagga ggcggatgcg aaatagctat gtcttgtgat    360
ataagaatag cttcaagcaa cgcaagattt ggtcaaccag aagtaggtct cggaataaca    420
cctggttttg gtggtacaca aagactttca gattagttg aatgggcat ggcaaagcag     480 cttatattta ctgcacaaaa tataaaggca gatgaagcat taagaatcgg acttgtaaat    540
aaggtagtag aacctagtga attaatgaat acagcaaaag aaattgcaaa caaaattgtg    600
agcaatgctc cagtagctgt taagttaagc aaacaggcta ttaatagagg aatgcagtgt    660
gatattgata ctgctttagc atttgaatca gaagcatttg gagaatgctt ttcaacagag    720
gatcaaaagg atgcaatgac agctttcata gagaaaagaa aaattgaagg cttcaaaaat    780
agatag                                                               786
```

```
<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 9
<211> LENGTH: 1197
<212> TYPE: DNA
<213> ORGANISM: Clostridium acetobutylicum

<400> SEQUENCE: 9
atgatagtaa aagcaaagtt tgtaaaagga tttatcagag atgtacatcc ttatggttgc      60
agaagggaag tactaaatca aatagattat tgtaagaagg ctattgggtt taggggacca     120
aagaaggttt taattgttgg agcctcatct gggtttggtc ttgctactag aatttcagtt     180
gcatttggag gtccagaagc tcacacaatt ggagtatcct atgaaacagg agctacagat     240
agaagaatag aacagcggga tggtataat aacatatttt ttaagaatt tgctaaaaaa       300 aaaggattag ttgcaaaaaa cttcattgag gatgcctttt ctaatgaaac caaagataaa     360
gttattaagt atataaagga tgaatttggt aaaatagatt tatttgttta gtttagct       420
```

```
gcgcctagga gaaaggacta taaaactgga aatgtttata cttcaagaat aaaaacaatt    480
ttaggagatt ttgagggacc gactattgat gttgaaagag acgagattac tttaaaaaag    540
gttagtagtg ctagcattga agaaattgaa gaaactagaa aggtaatggg tggagaggat    600
tggcaagagt ggtgtgaaga gctgctttat gaagattgtt tttcggataa agcaactacc    660
atagcatact cgtatatagg atccccaaga acctacaaga tatatagaga aggtactata    720
ggaatagcta aaaggatct tgaagataag gctaagctta taaatgaaaa acttaacaga    780
gttataggtg gtagagcctt tgtgtctgtg aataaagcat tagttacaaa agcaagtgca    840
tatattccaa cttttcctct ttatgcagct attttatata aggtcatgaa agaaaaaaat    900
attcatgaaa attgtattat gcaaattgag agaatgtttt ctgaaaaaat atattcaaat    960
gaaaaatac aatttgatga caagggaaga ttaaggatgg acgatttaga gcttagaaaa   1020
gacgttcaag acgaagttga tagaatatgg agtaatatta ctcctgaaaa ttttaaggaa   1080
ttatctgatt ataagggata caaaaaagaa ttcatgaact aaacggtttt tgatctagat   1140
ggggttgatt atagtaaaga cctggatata gaattattaa gaaaattaga acctaa      1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240
```

```
Gly Ile Ala Lys Lys Asp Leu Glu Asp Lys Ala Lys Leu Ile Asn Glu
            245                 250                 255

Lys Leu Asn Arg Val Ile Gly Gly Arg Ala Phe Val Ser Val Asn Lys
        260                 265                 270

Ala Leu Val Thr Lys Ala Ser Ala Tyr Ile Pro Thr Phe Pro Leu Tyr
    275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Lys Gly Arg Leu Arg Met Asp Asp Leu
            325                 330                 335

Glu Leu Arg Lys Asp Val Gln Asp Glu Val Asp Arg Ile Trp Ser Asn
        340                 345                 350

Ile Thr Pro Glu Asn Phe Lys Glu Leu Ser Asp Tyr Lys Gly Tyr Lys
    355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395

<210> SEQ ID NO 11
<211> LENGTH: 1407
<212> TYPE: DNA
<213> ORGANISM: Clostridium beijerinckii

<400> SEQUENCE: 11
atgaataaag acacactaat acctacaact aaagatttaa agtaaaaac aaatggtgaa      60 aacattaatt taaagaacta caaggataat tcttcatgtt tcggagtatt cgaaaatgtt     120
gaaaatgcta taagcagcgc tgtacacgca caaaagatat tatccttca ttatacaaaa      180 gagcaaagag aaaaaatcat aactgagata agaaggccg cattacaaaa taagagggtc     240
ttggctacaa tgattctaga agaaacacat atgggaagat atgaggataa aatattaaaa      300
catgaattgg tagctaaata tactcctggt acagaagatt taactactac tgcttggtca      360
ggtgataatg gtcttacagt tgtagaaatg tctccatatg gtgttatagg tgcaataact      420
ccttctacga atccaactga aactgtaata tgtaatagca taggcatgat agctgctgga      480
aatgctgtag tatttaacgg acacccatgc gctaaaaaat gtgttgcctt tgctgttgaa      540
atgataaata aggcaattat ttcatgtggc ggtcctgaaa tctagtaac aactataaaa      600 aatccaacta tggagtctct agatgcaatt attaagcatc cttcaataaa acttctttgc      660
ggaactgggg gtccaggaat ggtaaaaacc ctcttaaatt ctggtaagaa agctataggt      720
gctggtgctg gaaatccacc agttattgta gatgatactg ctgatataga aaaggctggt      780
aggagcatca ttgaaggctg ttctttttgat aataatttac cttgtattgc agaaaaagaa      840
gtatttgttt tgagaatgt tgcagatgat ttaatatccta acatgctaaa aaataatgct      900
gtaattataa atgaagatca agtatcaaaa ttaatagatt tagtattaca aaaaaataat      960
gaaactcaag aatactttat aaacaaaaaa tgggtaggaa aagatgcaaa attattctta     1020
gatgaaatag atgttgagtc tccttcaaat gttaaatgca taatctgcga agtaaatgca     1080
aatcatccat tgttatgac agaactcatg atgccaatat tgccaattgt aagagttaaa     1140
gatatagatg aagctattaa atatgcaaag atagcagaac aaaatagaaa acatagtgcc     1200
tatatttatt ctaaaaatat agacaaccta aatagatttg aaagagaaat agatactact     1260
```

-continued

```
attttttgtaa agaatgctaa atcttttgct ggtgttggtt atgaagcaga aggatttaca    1320
actttcacta ttgctggatc tactggtgag ggaataacct ctgcaaggaa ttttacaaga    1380
caaagaagat gtgtacttgc cggctaa                                        1407
```

<210> SEQ ID NO 12
<211> LENGTH: 468
<212> TYPE: PRT
<213> ORGANISM: Clostridium beijerinckii

<400> SEQUENCE: 12

```
Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350
```

```
Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 13
<211> LENGTH: 1215
<212> TYPE: DNA
<213> ORGANISM: Clostridium acetobutylicum

<400> SEQUENCE: 13
atggttgatt cgaatattc aataccaact agaattttt tcggtaaaga taagataaat        60
gtacttggaa gagagcttaa aaaatatggt tctaaagtgc ttatagttta tggtggagga      120
agtataaaga gaatggaat atatgataaa gctgtaagta tacttgaaaa aaacagtatt      180
aaattttatg aacttgcagg agtagagcca atccaagag taactacagt tgaaaaagga      240
gttaaaatat gtagagaaaa tggagttgaa gtagtactag ctataggtgg aggaagtgca     300
atagattgcg caaaggttat agcagcagca tgtgaatatg atggaaatcc atgggatatt     360
gtgttagatg ctcaaaaat aaaaagggtg cttcctatag ctagtatatt aaccattgct     420
gcaacaggat cagaaatgga tacgtgggca gtaataaata tatggatac aaacgaaaaa      480 ctaattgcgg cacatccaga tatggctcct aagttttcta tattagatcc aacgtatacg     540
tataccgtac ctaccaatca aacagcagca ggaacagctg atattatgag tcatatattt     600
gaggtgtatt ttagtaatac aaaaacagca tatttgcagg atagaatggc agaagcgtta     660
ttaagaactt gtattaaata tggaggaata gctcttgaga agccggatga ttatgaggca     720
agagccaatc taatgtgggc ttcaagtctt gcgataaatg acttttaac atatggtaaa     780 gacactaatt ggagtgtaca cttaatggaa catgaattaa gtgcttatta cgacataaca     840
cacggcgtag gcttgcaat tttaacacct aattggatgg agtatatttt aaataatgat     900
acagtgtaca gtttgttga atatggtgta atgtttggg aatagacaa agaaaaaaat      960 cactatgaca tagcacatca agcaatacaa aaaacaagag attactttgt aaatgtacta    1020
ggtttaccat ctagactgag agatgttgga attgaagaag aaaaattgga cataatggca    1080
aaggaatcag taaagcttac aggaggaacc ataggaaacc taagaccagt aaacgcctcc    1140
gaagtcctac aaatattcaa aaaatctgtg taaaacgcct ccgaagtcct acaaatattc    1200
aaaaaatctg tgtaa                                                    1215

<210> SEQ ID NO 14
<211> LENGTH: 390
<212> TYPE: PRT
<213> ORGANISM: Clostridium acetobutylicum
```

-continued

<400> SEQUENCE: 14

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390
```

<210> SEQ ID NO 15
<211> LENGTH: 1170
<212> TYPE: DNA
<213> ORGANISM: Clostridium acetobutylicum

<400> SEQUENCE: 15

```
atgctaagtt ttgattattc ataccaact aaagtttttt ttggaaaagg aaaaatagac      60
gtaattggag aagaaattaa gaaatatggc tcaagagtgc ttatagttta tggcggagga     120
agtataaaaa ggaacggtat atatgataga gcaacagcta tattaaaaga aaacaatata     180
gctttctatg aactttcagg agtagagcca atcctagga taacaacagt aaaaaaaggc     240
atagaaatat gtagagaaaa taatgtggat ttagtattag caatagggggg aggaagtgca     300
atagactgtt ctaaggtaat tgcagctgga gtttattatg atggcgatac atgggacatg     360
gttaaagatc catctaaaat aactaaagtt cttccaattg caagtatact tactcttttca     420
gcaacagggt ctgaaatgga tcaaattgca gtaatttcaa atatggagac taatgaaaag     480
cttggagtag acatgatga tatgagacct aaattttcag tgttagatcc tacatatact      540
tttacagtac ctaaaaatca aacagcagcg ggaacagctg acattatgag tcacaccttt      600
gaatcttact ttagtggtgt tgaaggtgct tatgtgcagg acggtatagc agaagcaatc     660
ttaagaacat gtataaagta tggaaaaata gcaatggaga agactgatga ttacgaggct     720
agagctaatt tgatgtgggc ttcaagttta gctataaatg gtctattatc acttggtaag     780
gatagaaaat ggagttgtca tcctatggaa cacgagttaa gtgcatatta tgatataaca     840
catggtgtag acttgcaat tttaacaccct aattggatgg aatatattct aaatgacgat     900
acacttcata atttgtttc ttatggaata atgtttggg aatagacaa gaacaaagat      960
aactatgaaa tagcacgaga ggctattaaa aatacgagaa aatactttaa ttcattgggt    1020
attccttcaa agcttagaga agttggaata ggaaaagata aactagaact aatggcaaag    1080
caagctgtta gaaattctgg aggaacaata ggaagtttaa gaccaataaa tgcagaggat    1140
gttcttgaga tatttaaaaa atcttattaa                                     1170
```

<210> SEQ ID NO 16
<211> LENGTH: 389
<212> TYPE: PRT
<213> ORGANISM: Clostridium acetobutylicum

<400> SEQUENCE: 16

```
Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125
```

```
Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
                180                 185                 190

Ala Asp Ile Met Ser His Thr Phe Glu Ser Tyr Phe Ser Gly Val Glu
                195                 200                 205

Gly Ala Tyr Val Gln Asp Gly Ile Ala Glu Ala Ile Leu Arg Thr Cys
210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
                260                 265                 270

Leu Ser Ala Tyr Tyr Asp Ile Thr His Gly Val Gly Leu Ala Ile Leu
                275                 280                 285

Thr Pro Asn Trp Met Glu Tyr Ile Leu Asn Asp Asp Thr Leu His Lys
290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
                340                 345                 350

Asp Lys Leu Glu Leu Met Ala Lys Gln Ala Val Arg Asn Ser Gly Gly
                355                 360                 365

Thr Ile Gly Ser Leu Arg Pro Ile Asn Ala Glu Asp Val Leu Glu Ile
370                 375                 380

Phe Lys Lys Ser Tyr
385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc     180 ggcaccttta atgagctgga cggggagctg atcgccttca gcagtcaggt ctatcagctg     240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca atcccctct gacaacctgt tctgcgccct gcgcatcgac     420
ggccatttcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggaccccgca gcatatgcag gggatcaacg tcgccgggta tcacgagcac     600
tttattaccg atgaccgcaa aggcggcggt cacctgctgg attaccagct cgaccatggg     660
```

```
gtgctgacct tcggcgaaat tcacaagctg atgatcgacc tgcccgccga cagcgcgttc      720
ctgcaggcta atctgcatcc cgataatctc gatgccgcca tccgttccgt agaaagttaa      780
```

<210> SEQ ID NO 18
<211> LENGTH: 259
<212> TYPE: PRT
<213> ORGANISM: Klebsiella pneumoniae

<400> SEQUENCE: 18

```
Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

<210> SEQ ID NO 19
<211> LENGTH: 1680
<212> TYPE: DNA
<213> ORGANISM: Klebsiella pneumoniae

<400> SEQUENCE: 19

```
atggacaaac agtatccggt acgccagtgg gcgcacggcg ccgatctcgt cgtcagtcag      60
ctggaagctc agggagtacg ccaggtgttc ggcatccccg cgccaaaat tgacaaggtc      120 ttcgactcac tgctggattc ctcgattcgc attattccgg tacgccacga agccaacgcc      180
gcgtttatgg ccgccgccgt cggacgcatt accggcaaag cgggcgtggc gctggtcacc      240
tccggtccgg gctgttccaa cctgatcacc ggcatggcca ccgcgaacag cgaaggcgac      300
```

```
ccggtggtgg ccctgggcgg cgcggtaaaa cgcgccgata agcgaagca ggtccaccag      360
agtatggata cggtggcgat gttcagcccg gtcaccaaat acgccgtcga ggtgacggcg      420
ccggatgcgc tggcggaagt ggtctccaac gccttccgcg ccgccgagca gggccggccg      480
ggcagcgcgt tcgttagcct gccgcaggat gtggtcgatg ccccggtcag cggcaaagtg      540
ctgccggcca gcggggcccc gcagatgggc gccgcgccgg atgatgccat cgaccaggtg      600
gcgaagctta tcgcccaggc gaagaacccg atcttcctgc tcggcctgat ggccagccag      660
ccggaaaaca gcaaggcgct gcgccgtttg ctggagacca gccatattcc agtcaccagc      720
acctatcagg ccgccggagc ggtgaatcag gataacttct ctcgcttcgc cggccggggtt      780
gggctgttta caaccaggc cggggaccgt ctgctgcagc tcgccgacct ggtgatctgc      840
atcggctaca gcccggtgga atacgaaccg gcgatgtgga acagcggcaa cgcgacgctg      900
gtgcacatcg acgtgctgcc cgcctatgaa gagcgcaact acaccccgga tgtcgagctg      960
gtgggcgata tcgccggcac tctcaacaag ctggcgcaaa atatcgatca tcggctggtg     1020
ctctccccgc aggcggcgga gatcctccgc gaccgccagc accagcgcga gctgctggac     1080
cgccgcggcg cgcagctgaa ccagtttgcc ctgcatccgc tgcgcatcgt tcgcgccatg     1140
caggacatcg tcaacagcga cgtcacgttg accgtggaca tgggcagctt ccatatctgg     1200
attgcccgct acctgtacag cttccgcgcc cgtcaggtga tgatctccaa cggccagcag     1260
accatgggcg tcgccctgcc ctgggctatc ggcgcctggc tggtcaatcc tgagcgaaaa     1320
gtggtctccg tctccggcga cggcggcttc ctgcagtcga gcatggagct ggagaccgcc     1380
gtccgcctga aagccaacgt actgcacctg atctgggtcg ataacggcta caacatggtg     1440
gccattcagg aagagaaaaa ataccagcgc ctgtccggcg tcgagttcgg gccgatggat     1500
tttaaagcct atgccgaatc cttcggcgcg aaagggtttg ccgtggaaag cgccgaggcg     1560
ctggagccga ccctgcacgc ggcgatggac gtcgacggcc cggcggtggt ggccattccg     1620
gtggattatc gcgataaccc gctgctgatg ggccagctgc atctgagtca gattctgtaa     1680

<210> SEQ ID NO 20
<211> LENGTH: 559
<212> TYPE: PRT
<213> ORGANISM: Klebsiella pneumoniae

<400> SEQUENCE: 20

Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140
```

```
Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
                260                 265                 270

Gln Leu Ala Asp Leu Val Ile Cys Ile Gly Tyr Ser Pro Val Glu Tyr
            275                 280                 285

Glu Pro Ala Met Trp Asn Ser Gly Asn Ala Thr Leu Val His Ile Asp
        290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
                340                 345                 350

Gln His Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
        370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555
```

<210> SEQ ID NO 21
<211> LENGTH: 771
<212> TYPE: DNA
<213> ORGANISM: Klebsiella pneumoniae

<400> SEQUENCE: 21

```
atgaaaaaag tcgcacttgt taccggcgcc ggccagggga ttggtaaagc tatcgccctt        60
cgtctggtga aggatggatt tgccgtggcc attgccgatt ataacgacgc caccgccaaa       120
gcggtcgcct cggaaatcaa ccaggccggc ggacacgccg tggcggtgaa agtggatgtc       180
tccgaccgcg atcaggtatt tgccgccgtt gaacaggcgc gcaaaacgct gggcggcttc       240
gacgtcatcg tcaataacgc cggtgtggca ccgtctacgc cgatcgagtc cattaccccg       300
gagattgtcg acaaagtcta caacatcaac gtcaaagggg tgatctgggg tattcaggcg       360
gcggtcgagg cctttaagaa agaggggcac ggcgggaaaa tcatcaacgc ctgttcccag       420
gccggccacg tcggcaaccc ggagctggcg gtgtatagct ccagtaaatt cgcggtacgc       480
ggcttaaccc agaccgccgc tcgcgacctc gcgccgctgg gcatcaccgt caacggctac       540
tgcccgggga ttgtcaaaac gccaatgtgg gccgaaattg accgccaggt gtccgaagcc       600
gccggtaaac cgctgggcta cggtaccgcc gagttcgcca aacgcatcac tctcggtcgt       660
ctgtccgagc cggaagatgt cgccgcctgc gtctcctatc ttgccagccc ggattctgat       720
tacatgaccg tcagtcgtt gctgatcgac ggcgggatgg tatttaacta a                 771
```

<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

```
        Thr Ala Glu Phe Ala Lys Arg Ile Thr Leu Gly Arg Leu Ser Glu Pro
            210                 215                 220

Glu Asp Val Ala Ala Cys Val Ser Tyr Leu Ala Ser Pro Asp Ser Asp
        225                 230                 235                 240

Tyr Met Thr Gly Gln Ser Leu Leu Ile Asp Gly Gly Met Val Phe Asn
                        245                 250                 255

<210> SEQ ID NO 23
<211> LENGTH: 1665
<212> TYPE: DNA
<213> ORGANISM: Klebsiella oxytoca

<400> SEQUENCE: 23
atgagatcga aaagatttga agcactggcg aaacgccctg tgaatcagga cggcttcgtt      60
aaggagtgga tcgaagaagg ctttatcgcg atggaaagcc cgaacgaccc aaaaccgtcg     120
attaaaatcg ttaacggcgc ggtgaccgag ctggacggga accggtaagc gattttgac      180 ctgatcgacc actttatcgc cgctacggt atcaacctga accgccga agaagtgatg       240 gcgatggatt cggtcaagct ggccaacatg ctgtgcgatc gaacgttaa acgcagcgaa     300 atcgtcccgc tgaccaccgc gatgacgccg gcgaaaattg tcgaagtggt ttcgcatatg     360
aacgtcgtcg agatgatgat ggcgatgcag aaaatgcgcg cccgccgcac cccgtcccag     420
caggcgcacg tcaccaacgt caaagataac ccggtacaga ttgccgccga cgccgccgaa     480
ggggcatggc gcggatttga cgaacaggaa accaccgttg cggtagcgcg ctatgcgccg     540
ttcaacgcca tcgcgctgct ggtgggctcg caggtaggcc gtccgggcgt gctgacgcag     600
tgctcgctgg aagaagccac cgagctgaag ctcggcatgc tgggccacac ctgctacgcc     660
gaaaccatct ccgtctacgg caccgagccg gtctttaccg acggcgacga cacgccgtgg     720
tcgaagggct cctcgcctc gtcctacgcc tctcgcgggc tgaaaatgcg ctttacctcc     780
ggctccggct cggaagtgca gatgggctac gccgaaggca aatccatgct ttatctggaa     840
gcgcgctgca tctacatcac caaagccgcg gcgtacagg gtctgcaaaa cggttccgta     900
agctgcatcg gcgtgccgtc tgcggtgcct tccggcattc gcgcggtgct ggcggaaaac     960
ctgatctgtt cgtcgctgga tctggagtgc gcctccagca acgaccagac cttcacccac    1020
tccgatatgc gtcgtaccgc gcgcctgctg atgcagttcc tgccgggcac cgactttatc    1080
tcctccggtt attccgcggt gccgaactac gacaacatgt cgccggctc caacgaagat     1140 gccgaagact ttgacgacta caacgtcatc cagcgcgacc tgaaggtgga cggcggtttg    1200
cgtccggttc gcgaagagga cgtcatcgcc atccgtaaca aagccgcccg cgcgctgcag    1260
gccgtgtttg ccgaatggg gctgccgccg attaccgatg aagaagttga agccgcgacc    1320
tacgcccacg gttcgaaaga tatgccggag cgcaacatcg tcgaagacat caagttcgcc    1380
caggaaatca tcaataaaaa ccgcaacggt ctggaagtgg tgaaagcgct ggcgcagggc    1440
ggattcaccg acgtggccca ggacatgctc aacatccaga aagctaagct gaccggggac    1500
tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                    1665

<210> SEQ ID NO 24
<211> LENGTH: 554
<212> TYPE: PRT
<213> ORGANISM: Klebsiella oxytoca
```

```
<400> SEQUENCE: 24

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415
```

```
Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550

<210> SEQ ID NO 25
<211> LENGTH: 675
<212> TYPE: DNA
<213> ORGANISM: Klebsiella oxytoca

<400> SEQUENCE: 25
atggaaatta atgaaaaatt gctgcgccag ataattgaag acgtgctcag cgagatgaag      60
ggcagcgata aaccggtctc gtttaatgcg ccggcggcct ccgcggcgcc ccaggccacg     120
ccgcccgccg cgacggcttc ctgacggaa gtgggcgaag cgcgtcaggg aacccagcag     180
gacgaagtga ttatcgccgt cggcccggct tcgggcctgg cgcagaccgt caatatcgtc     240
ggcatcccgc ataagagcat tttgcgcgaa gtcattgccg gtattgaaga agaaggcatt     300
aaggcgcgcg tgattcgctg ctttaaatcc tccgacgtgg ccttcgtcgc cgttgaaggt     360
aatcgcctga gcggctccgg catctctatc ggcatccagt cgaaaggcac cacggtgatc     420
caccagcagg gctgccgcc gctctctaac ctggagctgt ccccgcaggc gccgctgctg     480
accctggaaa cctatcgcca gatcggcaaa aacgccgccc gctatgcgaa acgcgaatcg     540
ccgcagccgg tcccgacgct gaatgaccag atggcgcggc cgaagtacca ggcgaaatcg     600
gccattttgc acattaaaga gaccaagtac gtggtgacgg gcaaaaaccc gcaggaactg     660
cgcgtggcgc tttga                                                     675

<210> SEQ ID NO 26
<211> LENGTH: 224
<212> TYPE: PRT
<213> ORGANISM: Klebsiella oxytoca

<400> SEQUENCE: 26

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60
```

```
Ile Ala Val Gly Pro Ala Phe Gly Leu Ala Gln Thr Val Asn Ile Val
 65                  70                  75                  80

Gly Ile Pro His Lys Ser Ile Leu Arg Glu Val Ile Ala Gly Ile Glu
                 85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220

<210> SEQ ID NO 27
<211> LENGTH: 522
<212> TYPE: DNA
<213> ORGANISM: Klebsiella oxytoca

<400> SEQUENCE: 27
atgaataccg acgcaattga atcgatggta cgcgacgtat tgagccgcat gaacagcctg      60
cagggcgagg cgcctgcggc ggctccggcg gctggcggcg cgtcccgtag cgccagggtc     120
agcgactacc cgctggcgaa caagcacccg gaatgggtga aaaccgccac caataaaacg     180
ctggacgact ttacgctgga aaacgtgctg agcaataaag tcaccgccca ggatatgcgt     240
attaccccgg aaaccctgcg cttacaggct tctattgcca agacgcgggg ccgcgaccgg     300
ctggcgatga acttcgagcg cgccgccgag ctgaccgcgg taccggacga tcgcattctt     360
gaaatctaca cgccctccgc ccctatcgc tcgacgaaag aggagctgct ggcgatcgcc      420
gacgatctcg aaagccgcta tcaggcgaag atttgcgccg ctttcgttcg cgaagcggcc     480
acgctgtacg tcgagcgtaa aaaactcaaa ggcgacgatt aa                       522

<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
  1               5                  10                  15

Met Asn Ser Leu Gln Gly Glu Ala Pro Ala Ala Ala Pro Ala Ala Gly
                 20                  25                  30

Gly Ala Ser Arg Ser Ala Arg Val Ser Asp Tyr Pro Leu Ala Asn Lys
             35                  40                  45

His Pro Glu Trp Val Lys Thr Ala Thr Asn Lys Thr Leu Asp Asp Phe
         50                  55                  60

Thr Leu Glu Asn Val Leu Ser Asn Lys Val Thr Ala Gln Asp Met Arg
 65                  70                  75                  80
```

```
Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
            165                 170

<210> SEQ ID NO 29
<211> LENGTH: 1041
<212> TYPE: DNA
<213> ORGANISM: Rhodococcus ruber

<400> SEQUENCE: 29
atgaaagccc tccagtacac cgagatcggc tccgagccgg tcgtcgtcga cgtccccacc        60
ccggcgcccg ggccgggtga gatcctgctg aaggtcaccg cggccggctt gtgccactcg       120
gacatcttcg tgatggacat gccggcagag cagtacatct acggtcttcc cctcacccct       180
ggccacgagg gcgtcggcac cgtcgccgaa ctcggcgccg cgtcaccgg attcgagacg        240 ggggacgccg tcgccgtgta cgggccgtgg ggtgcggtg cgtgccacgc gtgcgcgcgc        300
ggccgggaga actactgcac ccgcgccgcc gagctgggca tcaccccgcc cggtctcggc       360
tcgcccgggt cgatggccga gtacatgatc gtcgactcgg cgcgccacct cgtcccgatc       420
ggggacctcg acccgtcgc ggcggttccg ctcaccgacg cgggcctgac gccgtaccac        480
gcgatctcgc gggtcctgcc cctgctggga cccggctcga ccgcggtcgt catcggggtc       540
ggcggactcg gcacgtcgg catccagatc ctgcgcgccg tcagcgcggc ccgcgtgatc        600
gccgtcgatc tcgacgacga ccgactcgcg ctcgcccgcg aggtcggcgc cgacgcggcg       660
gtgaagtcgg cgccggggc ggcggacgcg atccgggagc tgaccggcgg tgagggcgcg        720
acggcggtgt cgacttcgt cggcgcccag tcgacgatcg acacggcgca gcaggtggtc       780
gcgatcgacg gcacatctc ggtggtcggc atccatgccg cgcccacgc caaggtcggc        840 ttcttcatga tcccgttcgg cgcgtccgtc gtgacgccgt actggggcac gcggtccgag       900
ctgatggacg tcgtggacct ggccgtgcc ggccggctcg acatccacac cgagacgttc        960
accctcgacg agggacccac ggcctaccgg cggctacgcg agggcagcat ccgcggccgc      1020
ggggtggtcg tcccgggctg a                                                1041

<210> SEQ ID NO 30
<211> LENGTH: 346
<212> TYPE: PRT
<213> ORGANISM: Rhodococcus ruber

<400> SEQUENCE: 30

Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45
```

```
Ala Glu Gln Tyr Ile Tyr Gly Leu Pro Leu Thr Leu Gly His Glu Gly
        50                  55                  60

Val Gly Thr Val Ala Glu Leu Gly Ala Gly Val Thr Gly Phe Glu Thr
 65                  70                  75                  80

Gly Asp Ala Val Ala Val Tyr Gly Pro Trp Gly Cys Gly Ala Cys His
                 85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Arg
        195                 200                 205

Leu Ala Leu Ala Arg Glu Val Gly Ala Asp Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Gly Ile His
        260                 265                 270

Ala Gly Ala His Ala Lys Val Gly Phe Phe Met Ile Pro Phe Gly Ala
    275                 280                 285

Ser Val Val Thr Pro Tyr Trp Gly Thr Arg Ser Glu Leu Met Asp Val
290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345

<210> SEQ ID NO 31
<211> LENGTH: 1476
<212> TYPE: DNA
<213> ORGANISM: Escherichia coli

<400> SEQUENCE: 31
atggctaact acttcaatac actgaatctg cgccagcagc tggcacagct gggcaaatgt        60
cgctttatgg ccgcgatga attcgccgat ggcgcgagct accttcaggg taaaaaagta       120
gtcatcgtcg gctgtggcgc acagggtctg aaccagggcc tgaacatgcg tgattctggt       180
ctcgatatct cctacgctct gcgtaaagaa gcgattgccg agaagcgcgc gtcctggcgt       240
aaagcgaccg aaaatggttt taagtgggt acttacgaag aactgatccc acaggcggat       300
ctggtgatta acctgacgcc ggacaagcag cactctgatg tagtgcgcac cgtacagcca       360
ctgatgaaag acggcgcggc gctgggctac tcgcacggtt tcaacatcgt cgaagtgggc       420
gagcagatcc gtaaagatat caccgtagtg atggttgcgc cgaaatgccc aggcaccgaa       480
```

```
gtgcgtgaag agtacaaacg tgggttcggc gtaccgacgc tgattgccgt tcacccggaa      540
aacgatccga aaggcgaagg catggcgatt gccaaagcct gggcggctgc aaccggtggt      600
caccgtgcgg gtgtgctgga atcgtccttc gttgcggaag tgaaatctga cctgatgggc      660
gagcaaacca tcctgtgcgg tatgttgcag gctggctctc tgctgtgctt cgacaagctg      720
gtggaagaag gtaccgatcc agcatacgca gaaaaactga ttcagttcgg ttgggaaacc      780
atcaccgaag cactgaaaca gggcggcatc accctgatga tggaccgtct ctctaacccg      840
gcgaaactgc gtgcttatgc gctttctgaa cagctgaaag agatcatggc accctgttc       900 cagaaacata tggacgacat catctccggc gaattctctt ccggtatgat ggcggactgg      960
gccaacgatg ataagaaact gctgacctgg cgtgaagaga ccggcaaaac cgcgtttgaa     1020
accgcgccgc agtatgaagg caaaatcggc gagcaggagt acttcgataa aggcgtactg     1080
atgattgcga tggtgaaagc gggcgttgaa ctggcgttcg aaaccatggt cgattccggc     1140
atcattgaag agtctgcata ttatgaatca ctgcacgagc tgccgctgat tgccaacacc     1200
atcgcccgta agcgtctgta cgaaatgaac gtggttatct ctgataccgc tgagtacggt     1260
aactatctgt tctcttacgc ttgtgtgccg ttgctgaaac cgtttatggc agagctgcaa     1320
ccgggcgacc tgggtaaagc tattccggaa ggcgcggtag ataacgggca actgcgtgat     1380
gtgaacgaag cgattcgcag ccatgcgatt gagcaggtag gtaagaaact gcgcggctat     1440
atgacagata tgaaacgtat tgctgttgcg ggttaa                               1476

<210> SEQ ID NO 32
<211> LENGTH: 491
<212> TYPE: PRT
<213> ORGANISM: Escherichia coli

<400> SEQUENCE: 32

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Lys Val Val Ile Val Gly Cys Gly Ala Gln
            35                  40                  45

Gly Leu Asn Gln Gly Leu Asn Met Arg Asp Ser Gly Leu Asp Ile Ser
        50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205
```

```
Ser Phe Val Ala Glu Val Lys Ser Asp Leu Met Gly Glu Gln Thr Ile
        210                 215                 220
Leu Cys Gly Met Leu Gln Ala Gly Ser Leu Leu Cys Phe Asp Lys Leu
225                 230                 235                 240
Val Glu Glu Gly Thr Asp Pro Ala Tyr Ala Glu Lys Leu Ile Gln Phe
                245                 250                 255
Gly Trp Glu Thr Ile Thr Glu Ala Leu Lys Gln Gly Gly Ile Thr Leu
            260                 265                 270
Met Met Asp Arg Leu Ser Asn Pro Ala Lys Leu Arg Ala Tyr Ala Leu
        275                 280                 285
Ser Glu Gln Leu Lys Glu Ile Met Ala Pro Leu Phe Gln Lys His Met
    290                 295                 300
Asp Asp Ile Ile Ser Gly Glu Phe Ser Ser Gly Met Met Ala Asp Trp
305                 310                 315                 320
Ala Asn Asp Asp Lys Lys Leu Leu Thr Trp Arg Glu Glu Thr Gly Lys
                325                 330                 335
Thr Ala Phe Glu Thr Ala Pro Gln Tyr Glu Gly Lys Ile Gly Glu Gln
            340                 345                 350
Glu Tyr Phe Asp Lys Gly Val Leu Met Ile Ala Met Val Lys Ala Gly
        355                 360                 365
Val Glu Leu Ala Phe Glu Thr Met Val Asp Ser Gly Ile Ile Glu Glu
    370                 375                 380
Ser Ala Tyr Tyr Glu Ser Leu His Glu Leu Pro Leu Ile Ala Asn Thr
385                 390                 395                 400
Ile Ala Arg Lys Arg Leu Tyr Glu Met Asn Val Ile Ser Asp Thr
                405                 410                 415
Ala Glu Tyr Gly Asn Tyr Leu Phe Ser Tyr Ala Cys Val Pro Leu Leu
            420                 425                 430
Lys Pro Phe Met Ala Glu Leu Gln Pro Gly Asp Leu Gly Lys Ala Ile
        435                 440                 445
Pro Glu Gly Ala Val Asp Asn Gly Gln Leu Arg Asp Val Asn Glu Ala
    450                 455                 460
Ile Arg Ser His Ala Ile Glu Gln Val Gly Lys Lys Leu Arg Gly Tyr
465                 470                 475                 480
Met Thr Asp Met Lys Arg Ile Ala Val Ala Gly
                485                 490

<210> SEQ ID NO 33
<211> LENGTH: 1851
<212> TYPE: DNA
<213> ORGANISM: Escherichia coli

<400> SEQUENCE: 33
atgcctaagt accgttccgc caccaccact catggtcgta atatggcggg tgctcgtgcg      60
ctgtggcgcg ccaccggaat gaccgacgcc gatttcggta agccgattat cgcggttgtg     120
aactcgttca cccaatttgt accgggtcac gtccatctgc gcgatctcgg taaactggtc     180
gccgaacaaa ttgaagcggc tggcggcgtt gccaaagagt caacaccat tgcggtggat     240 gatgggattg ccatgggcca cggggggatg ctttattcac tgccatctcg cgaactgatc     300
gctgattccg ttgagtatat ggtcaacgcc cactgcgccg acgccatggt ctgcatctct     360
aactgcgaca aaatcacccc ggggatgctg atggcttccc tgcgcctgaa tattccggtg     420
atctttgttt ccggcggccc gatggaggcc gggaaaacca acttccga tcagatcatc     480 aagctcgatc tggttgatgc gatgatccag ggcgcagacc cgaaagtatc tgactcccag     540
```

```
agcgatcagg ttgaacgttc cgcgtgtccg acctgcggtt cctgctccgg gatgtttacc      600
gctaactcaa tgaactgcct gaccgaagcg ctgggcctgt cgcagccggg caacggctcg      660
ctgctggcaa cccacgccga ccgtaagcag ctgttcctta atgctggtaa acgcattgtt      720
gaattgacca aacgttatta cgagcaaaac gacgaaagtg cactgccgcg taatatcgcc      780
agtaaggcgg cgtttgaaaa cgccatgacg ctggatatcg cgatgggtgg atcgactaac      840
accgtacttc acctgctggc ggcggcgcag gaagcggaaa tcgacttcac catgagtgat      900
atcgataagc tttcccgcaa ggttccacag ctgtgtaaag ttgcgccgag cacccagaaa      960
taccatatgg aagatgttca ccgtgctggt ggtgttatcg gtattctcgg cgaactggat     1020
cgcgcgggt tactgaaccg tgatgtgaaa aacgtacttg gcctgacgtt gccgcaaacg     1080
ctggaacaat acgacgttat gctgacccag gatgacgcgg taaaaaatat gttccgcgca     1140
ggtcctgcag gcattcgtac cacacaggca ttctcgcaag attgccgttg ggatacgctg     1200
gacgacgatc gcgccaatgg ctgtatccgc tcgctggaac acgcctacag caaagacggc     1260
ggcctggcgg tgctctacgg taactttgcg gaaaacggct gcatcgtgaa acggcaggc     1320
gtcgatgaca gcatcctcaa attcaccggc ccggcgaaaa tgtacgaaag ccaggacgat     1380
gcggtagaag cgattctcgg cggtaaagtt gtcgccggag atgtggtagt aattcgctat     1440
gaaggcccga aggcggtcc ggggatgcag gaaatgctct acccaaccag cttcctgaaa     1500
tcaatgggtc tcggcaaagc ctgtgcgctg atcaccgacg tcgtttctc tggtggcacc     1560
tctggtcttt ccatcggcca cgtctcaccg gaagcggcaa gcggcggcag cattggcctg     1620
attgaagatg gtgacctgat cgctatcgac atcccgaacc gtggcattca gttacaggta     1680
agcgatgccg aactggcggc gcgtcgtgaa gcgcaggacg ctcgaggtga caaagcctgg     1740
acgccgaaaa atcgtgaacg tcaggtctcc tttgccctgc gtgcttatgc cagcctggca     1800
accagcgccg acaaaggcgc ggtgcgcgat aaatcgaaac tggggggtta a              1851
```

<210> SEQ ID NO 34
<211> LENGTH: 616
<212> TYPE: PRT
<213> ORGANISM: Escherichia coli

<400> SEQUENCE: 34

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140
```

```
Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Ala Val Glu Ala
450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575
```

-continued

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615

<210> SEQ ID NO 35
<211> LENGTH: 1662
<212> TYPE: DNA
<213> ORGANISM: Lactococcus lactis

<400> SEQUENCE: 35

```
tctagacata tgtatactgt gggggattac ctgctggatc gcctgcacga actgggatt       60
gaagaaattt tcggtgtgcc aggcgattat aacctgcagt tcctggacca gattatctcg     120
cacaaagata tgaagtgggt cggtaacgcc aacgaactga cgcgagcta tggcagat        180
ggttatgccc gtaccaaaaa agctgctgcg tttctgacga cctttggcgt tggcgaactg     240
agcgccgtca acggactggc aggaagctac gccgagaacc tgccagttgt cgaaattgtt    300
gggtcgccta cttctaaggt tcagaatgaa ggcaaatttg tgcaccatac tctggctgat    360
ggggatttta acatttttat gaaaatgcat gaaccggtta ctgcggcccg cacgctgctg    420
acagcagaga atgctacggt tgagatcgac gcgtcctgt ctgcgctgct gaagagcgc      480
aagccggtat atatcaatct gcctgtcgat gttgccgcag cgaaagccga aaagccgtcg    540
ctgccactga aaaagaaaa cagcacctcc aatacatcgg accaggaaat tctgaataaa     600
atccaggaat cactgaagaa tgcgaagaaa ccgatcgtca tcaccggaca tgagatcatc    660
tcttttggcc tggaaaaaac ggtcacgcag ttcatttcta agaccaaact gcctatcacc    720
accctgaact tcggcaaatc tagcgtcgat gaagcgctgc cgagttttct gggtatctat    780
aatggtaccc tgtccgaacc gaacctgaaa gaattcgtcg aaagcgcgga ctttatcctg    840
atgctgggcg tgaaactgac ggatagctcc acaggcgcat ttacccacca tctgaacgag    900
aataaaatga tttcccctgaa tatcgacgaa ggcaaaatct ttaacgagcg catccagaac    960
ttcgattttg aatctctgat tagttcgctg ctggatctgt ccgaaattga gtataaaggt   1020
aaatatattg ataaaaaaca ggaggatttt gtgccgtcta atgcgctgct gagtcaggat   1080
cgtctgtggc aagccgtaga aaacctgaca cagtctaatg aaacgattgt tgcggaacag   1140
ggaacttcat ttttcggcgc ctcatccatt tttctgaaat ccaaaagcca tttcattggc   1200
caaccgctgt ggggagtat tggttatacc tttccggcgg cgctgggttc acagattgca   1260
gataaggaat cacgccatct gctgtttatt ggtgacggca gcctgcagct gactgtccag   1320
gaactggggc tggcgatccg tgaaaaaatc aatccgattt gctttatcat caataacgac   1380
ggctacaccg tcgaacgcga aattcatgga ccgaatcaaa gttacaatga catcccgatg   1440
tggaactata gcaaactgcc ggaatccttt ggcgcgacag aggatcgcgt ggtgagtaaa   1500
attgtgcgta cggaaaacga atttgtgtcg ttatgaaag aagcgcaggc tgacccgaat   1560
cgcatgtatt ggattgaact gatcctggca aagaaggcg caccgaaagt tctgaaaaag   1620
atggggaaac tgtttgcgga gcaaaataaa agctaaggat cc                      1662
```

<210> SEQ ID NO 36
<211> LENGTH: 548
<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415
```

-continued

```
Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

<210> SEQ ID NO 37
<211> LENGTH: 1164
<212> TYPE: DNA
<213> ORGANISM: Escherichia coli

<400> SEQUENCE: 37

```
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg cacattctg      360
caaacgggcg taaagagat aaaagcgcc atcccgatgg ctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacacccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc taatcgaaga tggtccgaaa gccctgaaag agccagaaaa ctacgatgtg     720
cgcgccaacg tcatgtgggc ggcgactcag gcgctgaacg gtttgattgg cgctggcgta     780
ccgcaggact gggcaacgca tatgctgggc cacgaactga ctgcgatgca cggtctggat     840
cacgcgcaaa cactggctat cgtcctgcct gcactgtgga tgaaaaacg cgataccaag     900
cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa atcatgaca ttacgttgga tgtcagccgc    1140
cgtatatacg aagccgcccg ctaa                                             1164
```

<210> SEQ ID NO 38
<211> LENGTH: 387
<212> TYPE: PRT
<213> ORGANISM: Escherichia coli

<400> SEQUENCE: 38

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Ser Val Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
    275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
    355                 360                 365

Gly Glu Asn His Asp Ile Thr Leu Asp Val Ser Arg Arg Ile Tyr Glu
370                 375                 380

Ala Ala Arg
385
```

```
<210> SEQ ID NO 39
<211> LENGTH: 19
<212> TYPE: DNA
<213> ORGANISM: Artificial Sequence
<220> FEATURE:
<223> OTHER INFORMATION: Primer HK12

<400> SEQUENCE: 39
gagtttgatc ctggctcag                                              19

<210> SEQ ID NO 40
<211> LENGTH: 16
<212> TYPE: DNA
<213> ORGANISM: Artificial Sequence
<220> FEATURE:
<223> OTHER INFORMATION: Primer HK13

<400> SEQUENCE: 40
taccttgtta cgactt                                                 16

<210> SEQ ID NO 41
<211> LENGTH: 15
<212> TYPE: DNA
<213> ORGANISM: Artificial Sequence
<220> FEATURE:
<223> OTHER INFORMATION: Primer JCR14

<400> SEQUENCE: 41
acgggcggtg tgtac                                                  15

<210> SEQ ID NO 42
<211> LENGTH: 16
<212> TYPE: DNA
<213> ORGANISM: Artificial Sequence
<220> FEATURE:
<223> OTHER INFORMATION: Primer JCR15

<400> SEQUENCE: 42
gccagcagcc gcggta                                                 16

<210> SEQ ID NO 43
<211> LENGTH: 1485
<212> TYPE: DNA
<213> ORGANISM: Pediococcus pentosaceus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (1282)..(1282)
<223> OTHER INFORMATION: n is a, c, g, or t
<220> FEATURE:
<221> NAME/KEY: misc_feature
<222> LOCATION: (1484)..(1484)
<223> OTHER INFORMATION: n is a, c, g, or t

<400> SEQUENCE: 43
cantctgtca ccttagacgg ctagctccta aaaggttacc ccaccggctt tgggtgttac    60
aaactctcat ggtgtgacgg gcggtgtgta caaggcccgg gaacgtattc accgcggcat   120
gctgatccgc gattactagc gattccgact tcgtgtaggc gagttgcagc ctacagtccg   180
aactgagaat ggttttaaga gattagctta acctcgcggt ctcgcgactc gttgtaccat   240
ccattgtagc acgtgtgtag cccaggtcat aaggggcatg atgatttgac gtcgtcccca   300
ccttcctccg gtttgtcacc ggcagtctca ctagagtgcc caacttaatg ctggcaacta   360
gtaataaggg ttgcgctcgt tgcgggactt aacccaacat ctcacgacac gagctgacga   420
```

```
caaccatgca ccacctgtca ttctgtcccc gaagggaacc tctaatctct tagactgtca      480
gaagatgtca agacctggta aggttcttcg cgtagcttcg aattaaacca catgctccac      540
cgcttgtgcg ggccccgtc aattcttttg agtttcaacc ttgcggtcgt actcccagg       600 cggattactt aatgcgttag ctgcagcact gaagggcgga aaccctccaa cacttagtaa      660
tcatcgttta cggcatggac taccagggta tctaatcctg ttcgctaccc atgctttcga      720
gcctcagcgt cagttgcaga ccagacagcc gccttcgcca ctggtgttct tccatatatc      780
tacgcatttc accgctacac atggagttcc actgtcctct tctgcactca gtctcccag       840 tttccaatgc acttcttcgg ttgagccgaa ggctttcaca ttagacttaa agaccgcct       900 gcgctcgctt tacgcccaat aaatccggat aacgcttgcc acctacgtat taccgcggct      960
gctggcacgt agttagccgt ggcttttctgg ttaaataccg tcactgggta aacagttact    1020
cttacccacg ttcttcttta acaacagagc tttacgagcc gaaacccttc ttcactcacg     1080
cggcgttgct ccatcagact tgcgtccatt gtggaagatt ccctactgct gcctcccgta     1140
ggagtctggg ccgtgtctca gtcccaatgt ggccgattac cctctcaggt cggctacgta     1200
tcactgcctt ggtgagcctt tacctcacca actagctaat acgccgcggg tccatccaga    1260
agtgatagca gagccatctt tnaaaagaaa accatgcggt tttctctgtt atacggtatt    1320
agcatctgtt tccaggtgtt atcccctact tctgggcagg ttacccacgt gttactcacc    1380
cgttcgccac tcacttcgtg ttaaaatctc aatcagtaca agtacgtcat aatcaattaa    1440
cggaagttcg ttcgacttgc atgtataggc acgccgccag cgtnc                   1485
```

```
<210> SEQ ID NO 44
<211> LENGTH: 1483
<212> TYPE: DNA
<213> ORGANISM: Pediococcus acidilactici
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (1443)..(1443)
<223> OTHER INFORMATION: n is a, c, g, or t
<220> FEATURE:
<221> NAME/KEY: misc_feature
<222> LOCATION: (1474)..(1474)
<223> OTHER INFORMATION: n is a, c, g, or t
<220> FEATURE:
<221> NAME/KEY: misc_feature
<222> LOCATION: (1481)..(1481)
<223> OTHER INFORMATION: n is a, c, g, or t

<400> SEQUENCE: 44
gacgctggcg gcgtgcctat catgcaagtc gaacgaactt ccgttaattg attatgacgt       60
gcttgcactg aatgagattt taacacgaag tgagtggcgg acgggtgagt aacacgtggg      120
taacctgccc agaagtaggg gataacacct ggaaacagat gctaataccg tataacagag      180
aaaaccgcct ggttttcttt taaaagatgg ctctgctatc acttctggat ggacccgcgg      240
cgcattagct ngttggtgag gtaacggctc accaaggcga tgatgcgtag ccgacctgag      300
agggtaatcg gccacattgg gactgagaca cggcccagac tcctacggga ggcagcagta     360
gggaatcttc cacaatggac gcaagtctga tggagcaacg ccgcgtgagt gaagaagggt     420
ttcggctcgt aaagctctgt tgttaaagaa gaacgtgggt gagagtaact gttcacccag     480
tgacggtatt taaccagaaa gccacggcta actacgtgcc agcagccgcg gtaatacgta     540
ggtggcaagc gttatccgga tttattgggc gtaaagcgag cgcaggcggt ctttttaagtc    600
```

-continued

```
taatgtgaaa gccttcggct caaccgaaga agtgcattgg aaactgggag acttgagtgc        660
agaagaggac agtggaactc catgtgtagc ggtgaaatgc gtagatatat ggaagaacac        720
cagtggcgaa ggcggctgtc tggtctgtaa ctgacgctga ggctcgaaag catgggtagc        780
gaacaggatt agataccctg gtagtccatg ccgtaaacga tgattactaa gtgttggagg        840
gtttccgccc ttcagtgctg cagctaacgc attaagtaat ccgcctgggg agtacgaccg        900
caaggttgaa actcaaaaga attgacgggg gcccgcacaa gcggtggagc atgtggttta        960
attcgaagct acgcgaagaa ccttaccagg tcttgacatc ttctgccaac ctaagagatt       1020
aggcgttccc ttcggggaca gaatgacagg tggtgcatgg ttgtcgtcag ctcgtgtcgt       1080
gagatgttgg gttaagtccc gcaacgagcg caaccettat tactagttgc cagcattcag       1140
ttgggcactc tagtgagact gccggtgaca aaccggagga aggtggggac gacgtcaaat       1200
catcatgccc cttatgacct gggctacaca cgtgctacaa tggatggtac aacgagtcgc       1260
gaaaccgcga ggtttagcta atctcttaaa accattctca gttcggactg taggctgcaa       1320
ctcgcctaca cgaagtcgga atcgctagta atcgcggatc agcatgccgc ggtgaatacg       1380
ttcccgggcc ttgtacacac cgcccgtcac accatgagag tttgtaacac ccaaagccgg       1440
tgnggtaacc ttttaggagc tagccgtcta aggngacaga ntg                        1483
```

SOLVENT TOLERANT MICROORGANISMS

FIELD OF THE INVENTION

The invention relates to the field of industrial microbiology. Specifically, microorganisms have been isolated that demonstrate high tolerance to alcohols, particularly butanols.

BACKGROUND OF THE INVENTION

Butanol is an important industrial chemical, useful as a fuel additive, as a feedstock chemical in the plastics industry, and as a food-grade extractant in the food and flavor industry. Each year 10 to 12 billion pounds of butanol are produced by petrochemical means and the need for this commodity chemical will likely increase.

Methods for the chemical synthesis of butanols are known. For example, 1-butanol may be produced using the Oxo process, the Reppe process, or the hydrogenation of crotonaldehyde (*Ullmann's Encyclopedia of Industrial Chemistry*, 6$^{th}$ edition, 2003, Wiley-VCH Verlag GmbH and Co., Weinheim, Germany, Vol. 5, pp. 716-719). 2-Butanol may be produced using n-butene hydration (*Ullmann's Encyclopedia of Industrial Chemistry*, 6$^{th}$ edition, 2003, Wiley-VCH Verlag GmbH and Co., Weinheim, Germany, Vol. 5, pp. 716-719). Additionally, isobutanol may be produced using Oxo synthesis, catalytic hydrogenation of carbon monoxide (*Ullmann's Encyclopedia of Industrial Chemistry*, 6$^{th}$ edition, 2003, Wiley-VCH Verlag GmbH and Co., Weinheim, Germany, Vol. 5, pp. 716-719) or Guerbet condensation of methanol with n-propanol (Carlini et al., *J. Molec. Catal. A: Chem.* 220:215-220 (2004)). These processes use starting materials derived from petrochemicals and are generally expensive and are not environmentally friendly.

Methods of producing butanol by fermentation are also known, where the most popular process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Additionally, recombinant microbial production hosts expressing a 1-butanol biosynthetic pathway (Donaldson et al., copending and commonly owned U.S. patent application Ser. No. 11/527,995), a 2-butanol biosynthetic pathway (Donaldson et al., copending and commonly owned U.S. Patent Application No. 60/796,816, and an isobutanol biosynthetic pathway (Maggio-Hall et al., copending and commonly owned U.S. patent application Ser. No. 11/586,315) have been described. However, biological production of butanols is believed to be limited by butanol toxicity to the host microorganism used in the fermentation.

Strains of *Clostridium* that are tolerant to 1-butanol have been isolated by chemical mutagenesis (Jain et al. U.S. Pat. No. 5,192,673; and Blaschek et al. U.S. Pat. No. 6,358,717), overexpression of certain classes of genes such as those that express stress response proteins (Papoutsakis et al. U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., Current Microbiology 14(5):295-299 (1987)). Desmond et al. (*Appl. Environ. Microbiol.* 70(10):5929-5936 (2004)) report that overexpression of GroESL, a stress response protein, in *Lactococcus lactis* and *Lactobacillus paracasei* produced strains that were able to grow in the presence of 0.5% volume/volume (v/v) [0.4% weight/volume (w/v)] 1-butanol. Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) have been described. Additionally, some *Lactobacillus* species are known to be tolerant to ethanol (see for example, Couto et al., *Biotechnol. Lett.* 19:487-490 (1997) and Ingram et al. *Adv. Microbial. Physiol.* 25:253-300 (1984)). However, for most microorganisms described in the art, growth is totally inhibited at a concentration of less than 2.0% w/v 1-butanol when grown in a liquid medium at 37° C. Moreover, microbial strains that have a tolerance to 2-butanol and isobutanol are not known in the art. Therefore, microorganisms that have a high tolerance to 1-butanol, 2-butanol, and isobutanol would represent an advance in the art.

There is a need, therefore, for microbial host strains that are more tolerant to butanols and may be used for the bioproduction of butanols to high titer. The present invention addresses this need through the discovery of butanol tolerant microorganisms.

BRIEF DESCRIPTION OF FIGURES, BIOLOGICAL DEPOSITS AND SEQUENCE DESCRIPTIONS

The various embodiments of the invention can be more fully understood from the following detailed description, figures, biological deposits, and the accompanying sequence descriptions, which form a part of this application.

Figure 1:
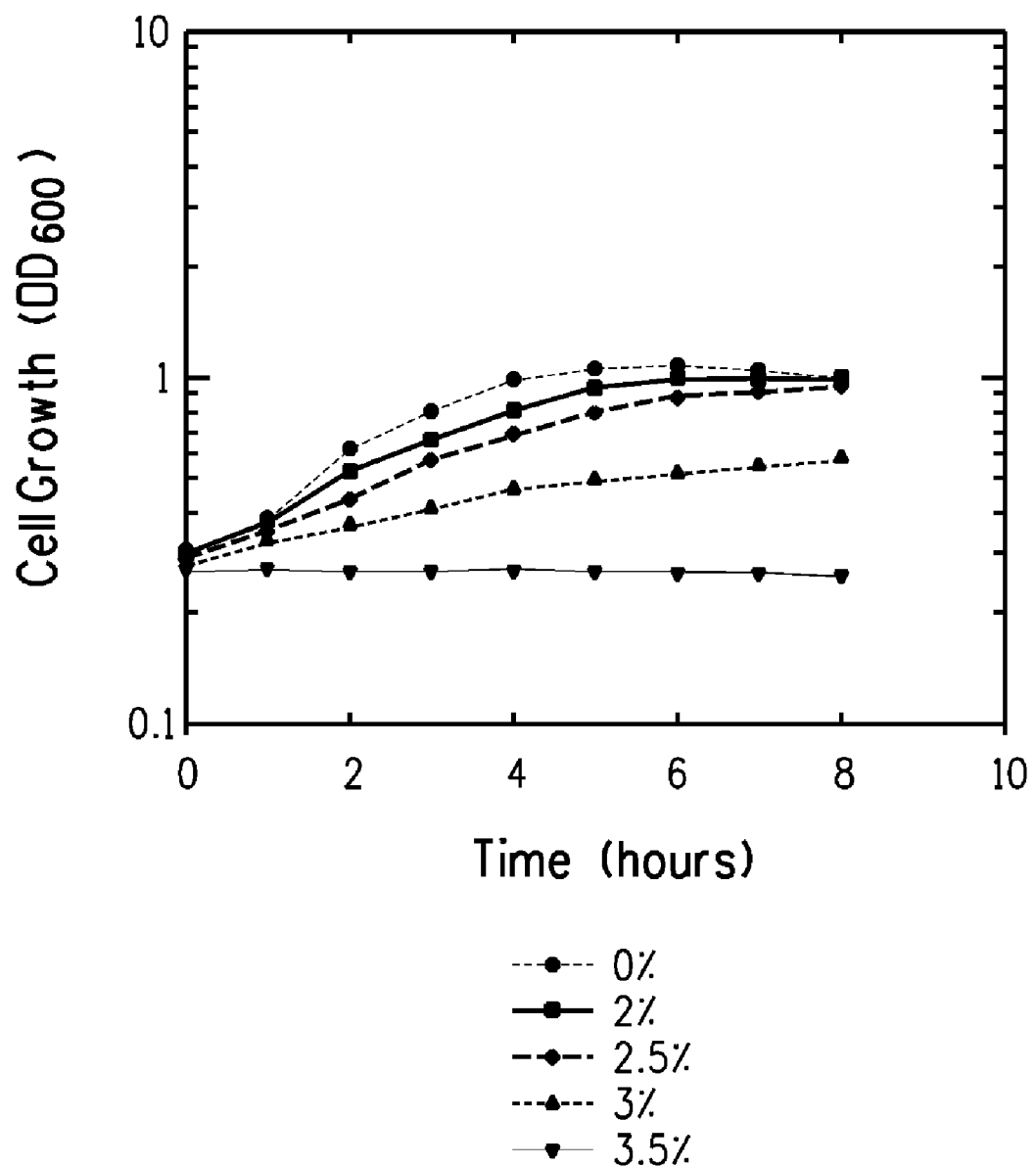
FIG. 1 shows the growth of *Pediococcus pentosaceus* strain PN1011 in liquid medium containing 1-butanol at 37° C.

Applicants made the following biological deposits with an international depository (American Type Culture Collection (ATCC), 10801 University Blvd., Manassas, Va. 20110-2209, USA) under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Pediococcus pentosaceus* PN1011 | ATCC: PTA-8068 | Dec. 7, 2006 |
| *Pediococcus acidilactici* PN1042 | ATCC: PTA-8069 | Dec. 7, 2006 |

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |

TABLE 1-continued

Summary of Gene and Protein SEQ ID Numbers
for 1-Butanol Biosynthetic Pathway

| Description | SEQ ID NO: Nucleic acid | SEQ ID NO: Peptide |
|---|---|---|
| Acetyl-CoA acetyltransferase thlB from *Clostridium acetobutylicum* ATCC 824 | 3 | 4 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| Butanol dehydrogenase bdhB from *Clostridium acetobutylicum* ATCC 824 | 13 | 14 |
| Butanol dehydrogenase bdhA from *Clostridium acetobutylicum* ATCC 824 | 15 | 16 |

TABLE 2

Summary of Gene and Protein SEQ ID Numbers
for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Gene and Protein SEQ ID Numbers
for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *E. coli* ilvC (acetohydroxy acid reductoisomerase) | 31 | 32 |
| *E. coli* ilvD (acetohydroxy acid dehydratase) | 33 | 34 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

SEQ ID NOs:39 and 40 are the nucleotide sequences of primers used to amplify the 16S rRNA genes of butanol tolerant strains, as described in Example 1.

SEQ ID NOs:41 and 42 are the nucleotide sequences of primers used to sequence the amplified 16S rRNA genes of butanol tolerant strains, as described in Example 1.

SEQ ID NOs:43 and 44 are the nucleotide sequences of the 16S rRNA genes of butanol tolerant *Pediococcus* strains, identified as described in Example 1.

DETAILED DESCRIPTION OF THE INVENTION

The present invention provides microorganisms that demonstrate high tolerance to alcohols, particularly butanols. The microorganisms of the invention are capable of low levels of growth in the presence of 3.0% w/v 1-butanol in a liquid medium at 37° C. These butanol tolerant microorganisms may be genetically engineered to comprise a butanol biosynthetic pathway and used for the bioproduction of 1-butanol, 2-butanol, or isobutanol to high titer.

The following definitions and abbreviations are to be used for the interpretation of the claims and the specification.

The term "invention" or "present invention" as used herein is a non-limiting term and is not intended to refer to any single embodiment of the particular invention but encompasses all possible embodiments as described in the specification and the claims.

The term "butanol" as used herein, refers to 1-butanol, 2-butanol, isobutanol, or mixtures thereof.

The terms "butanol tolerant microorganism" and "tolerant" when used to describe a microorganism of the invention, refers to a bacterium or yeast that exhibits growth in the presence of 2.5% w/v or greater 1-butanol, 2-butanol, or isobutanol when grown on a solid medium at 37° C., or in the presence 2.0% w/v or greater 1-butanol, 2-butanol, or isobutanol when grown in a liquid medium at 37° C.

The term "carbon substrate" or "fermentable carbon substrate" refers to a carbon source capable of being metabolized by the butanol tolerant microorganisms of the present invention and particularly carbon sources selected from the group consisting of monosaccharides, oligosaccharides, polysaccharides, and one-carbon substrates or mixtures thereof.

The term "aerobic conditions" means growth conditions in the presence of oxygen.

The term "anaerobic conditions" means growth conditions in the absence of oxygen.

The term "microaerophilic conditions" means growth conditions with low levels of oxygen (i.e., below normal atmospheric oxygen levels).

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and H₂O. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called transenoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "butanol dehydrogenase" refers to an enzyme that catalyzes the conversion of butyraldehyde to 1-butanol, using NADH or NADPH as cofactor. Butanol dehydrogenases are available from, for example, *C. acetobutylicum* (GenBank NOs: NP_149325, NC_001988; NP_349891 (SEQ ID NO:14), NC_003030 (SEQ ID NO:13); and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate. Suitable acetolactate synthase enzymes are available from a number of sources, for example, *Bacillus subtilis* (GenBank Nos: AAA22222 NCBI (National Center for Biotechnology Information) amino acid sequence, L04470 NCBI nucleotide sequence), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-Butanol dehydrogenases are a subset of the broad family of alcohol dehydrogenases. 2-Butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), *C. acetobutylicum* (GenBank Nos: NP_349892, NC_003030) and *C. acetobutylicum* (GenBank NOs: NP_349891 (SEQ ID NO:14), NC_003030 (SEQ ID NO:13).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

In one embodiment, the present invention provides microorganisms belonging to the genus *Pediococcus* that demonstrate high tolerance to alcohols, particularly butanols. The microorganisms of the invention are capable of low levels of growth in the presence of 3.0% w/v 1-butanol in a liquid medium at 37° C. These butanol tolerant microorganisms may be genetically engineered to comprise a butanol biosynthetic pathway and used for the bioproduction of 1-butanol, 2-butanol, or isobutanol to high titer.

Butanol Tolerant Microorganisms

The butanol tolerant microorganisms of the invention were identified by screening a private culture collection containing lactic acid bacteria for growth on 1-butanol, as described in Example 1, below. The bacterial strains in the collection were plated onto an agar medium which contained up to 3.5% weight/volume (w/v) 1-butanol and cultured for 24 hours at 37° C. The most tolerant strains were identified by additional testing in liquid broth containing various amounts of 1-butanol. The butanol tolerant strains were identified using 16S ribosomal RNA (rRNA) gene sequencing.

Two of the butanol tolerant strains were identified as members of the genus *Pediococcus*, specifically *Pediococcus pentosaceus* ATCC No. PTA-8068 (PN1011), and *Pediococcus acidilactici* ATCC No. PTA-8069 (PN1042). All of these strains displayed low levels of growth in a liquid medium containing 3.0% (w/v) 1-butanol at 37° C.

The isolated butanol tolerant *Pediococcus* strains may be genetically engineered to comprise genetic constructs encoding a butanol biosynthetic pathway and grown under suitable conditions to produce butanol. The butanol biosynthetic pathway may be a 1-butanol, 2-butanol, or isobutanol biosynthetic pathway.

1-Butanol Biosynthetic Pathway

A biosynthetic pathway for the production of 1-butanol is described by Donaldson et al. in copending and commonly owned U.S. patent application Ser. No. 11/527,995, which is incorporated herein by reference. This biosynthetic pathway comprises the following substrate to product conversions:

a) acetyl-CoA to acetoacetyl-CoA, as catalyzed for example by acetyl-CoA acetyltransferase encoded by the genes given as SEQ ID NO:1 or 3;

b) acetoacetyl-CoA to 3-hydroxybutyryl-CoA, as catalyzed for example by 3-hydroxybutyryl-CoA dehydrogenase encoded by the gene given as SEQ ID NO:5;

c) 3-hydroxybutyryl-CoA to crotonyl-CoA, as catalyzed for example by crotonase encoded by the gene given as SEQ ID NO:7;

d) crotonyl-CoA to butyryl-CoA, as catalyzed for example by butyryl-CoA dehydrogenase encoded by the gene given as SEQ ID NO:9;

e) butyryl-CoA to butyraldehyde, as catalyzed for example by butyraldehyde dehydrogenase encoded by the gene given as SEQ ID NO:11; and f) butyraldehyde to 1-butanol, as catalyzed for example by butanol dehydrogenase encoded by the genes given as SEQ ID NO:13 or 15.

The pathway requires no ATP and generates $NAD^+$ and/or $NADP^+$, thus, balances with the central, metabolic routes that generate acetyl-CoA. metabolism.

2-Butanol Biosynthetic Pathway

Biosynthetic pathways for the production of 2-butanol are described by Donaldson et al. in copending and commonly owned U.S. Patent Application No. 60/796,816, which is incorporated herein by reference. One 2-butanol biosynthetic pathway comprises the following substrate to product conversions:

a) pyruvate to alpha-acetolactate, as catalyzed for example by acetolactate synthase encoded by the gene given as SEQ ID NO:19;

b) alpha-acetolactate to acetoin, as catalyzed for example by acetolactate decarboxylase encoded by the gene given as SEQ ID NO:17;

c) acetoin to 2,3-butanediol, as catalyzed for example by butanediol dehydrogenase encoded by the gene given as SEQ ID NO:21;

d) 2,3-butanediol to 2-butanone, catalyzed for example by butanediol dehydratase encoded by genes given as SEQ ID NOs:23, 25, and 27; and e) 2-butanone to 2-butanol, as catalyzed for example by 2-butanol dehydrogenase encoded by the gene given as SEQ ID NO:29.

Isobutanol Biosynthetic Pathway

Biosynthetic pathways for the production of isobutanol are described by Maggio-Hall et al. in copending and commonly owned U.S. patent application Ser. No. 11/586,315, which is incorporated herein by reference. One isobutanol biosynthetic pathway comprises the following substrate to product conversions:

a) pyruvate to acetolactate, as catalyzed for example by acetolactate synthase encoded by the gene given as SEQ ID NO:19;

b) acetolactate to 2,3-dihydroxyisovalerate, as catalyzed for example by acetohydroxy acid isomeroreductase encoded by the gene given as SEQ ID NO:31;

c) 2,3-dihydroxyisovalerate to α-ketoisovalerate, as catalyzed for example by acetohydroxy acid dehydratase encoded by the gene given as SEQ ID NO:33;

d) α-ketoisovalerate to isobutyraldehyde, as catalyzed for example by a branched-chain keto acid decarboxylase encoded by the gene given as SEQ ID NO:35; and e) isobutyraldehyde to isobutanol, as catalyzed for example by a branched-chain alcohol dehydrogenase encoded by the gene given as SEQ ID NO:37 or SEQ ID NO:13.

Construction of *Pediococcus* Hosts for Butanol Production

Recombinant, butanol tolerant *Pediococcus* strains containing the necessary genes that will encode one of the enzymatic pathways for the conversion of a fermentable carbon substrate to butanol may be constructed using techniques well known in the art. The genome sequence of *Pediococcus pentosaceus* is known (National Center for Biotechnology Information (NCBI) database), GenBank™ identification as follows:

*Pediococcus pentosaceus* ATCC 25745, complete genome gi|116491818|ref|NC_008525.1|[116491818]

Members of the genus *Pediococcus* have a G+C content ranging from 32% to 42%.

In the present invention, genes encoding the enzymes of one of the butanol biosynthetic pathways described above may be isolated from various sources (see above). Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available.

Once the relevant pathway genes are identified and isolated they may be transformed into a butanol tolerant *Pediococcus* host by means well known in the art. Vectors or cassettes useful for the transformation of *Pediococcus* are known (see below). Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific production host.

Initiation control regions or promoters, which are useful to drive expression of the relevant pathway coding regions in the desired *Pediococcus* host cell, may be obtained from species of *Pediococcus*, other lactic acid bacteria, or other Gram-positive organisms. Non-limiting examples are the idhD promoter from *Pediococcus acidilactici* (Garmyn et al., *J. Bacteriol.* 177:3427-3437 (1995)) and the ldhL promoter from *Pediococcus acidilactici* (Garmyn et al., *Appl. Environ. Microbiol.* 61:266-272 (1995)). Termination control regions may also be derived from various genes native to the preferred hosts or related bacteria. Optionally, a termination site may be unnecessary, however, it is most preferred if included.

The *Pediococcus* genus belongs to the Lactobacillales family and many plasmids and vectors used in the transformation of *Bacillus subtilis* and *Streptococcus* may be used for *Pediococcus*. A non-limiting example of a suitable vector is pHPS9 (Bukhtiyarova et al. *Appl. Environ. Microbiol.* 60:3405-3408 (1994)). Several plasmids from *Pediococcus* have also been reported (Alegre et al., *FEMS Microbiol. Lett.* 250:151-156 (2005); Shareck et al. *Crit. Rev Biotechnol.* 24:155-208 (2004)).

The various genes for a butanol biosynthetic pathway may be assembled into any suitable vector, such as those described above. The codons can be optimized for expression based on the codon index deduced from the genome sequence of *Pediococcus pentosaceus*. The plasmids may be introduced into the host cell using methods known in the art, such as electroporation (see for example, Osmanagaoglu et al., *J. Basic Microbiol.* 40:233-241 (2000); Alegre et al., *FEMS Microbiol. Lett.* 250:151-156 (2005)). Plasmids can also be introduced into *Pediococcus* by conjugation (Gonzalez and Kunka, *Appl. Environ. Microbiol.* 46:81-89 (1983)). The butanol biosynthetic pathway genes can also be integrated into the chromosome of *Pediococcus* using integration vectors (Davidson et al. *Antonie van Leeuwenhoek* 70:161-183 (1996)).

Fermentation Media

Fermentation media for the production of butanol must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 25° C. to about 40° C. in an appropriate medium. Suitable growth media in the present invention are common commercially prepared media such as Bacto Lactobacilli MRS broth or Agar (Difco), Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerophilic conditions are preferred.

Industrial Batch and Continuous Fermentations

Butanol may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227 (1992), herein incorporated by reference.

Butanol may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol may be practiced using either batch, fed-batch or continuous processes and that any known mode of fermentation would be suitable. Additionally, it is contemplated that cells may be immobilized on a substrate as whole cell catalysts and subjected to fermentation conditions for butanol production.

Methods for Butanol Isolation from the Fermentation Medium

The bioproduced butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec' means second(s), "μL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmol" means micromole(s), "g" means gram(s), "μg" means microgram(s), "mg" means milligram(s), "rpm" means revolutions per minute, "w/v" means weight/volume, "OD" means optical density, "$OD_{600}$" means optical density measured at a wavelength of 600 nm, "$OD_{595}$" means optical density measured at a wavelength of 595 nm, "$IC_{50}$" means the concentration of butanol that causes a 50% inhibition of growth, "GCMS" means gas chromatography-mass spectrometry, and "HPLC" means high performance liquid chromatography.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory Press, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1

Identification of Butanol Tolerant Bacterial Strains in a Culture Collection

The purpose of this Example was to identify butanol tolerant bacteria that were present in a private culture collection that contained many different strains of lactic acid bacteria. Each member of the collection was tested for growth in media containing 1-butanol. Several 1-butanol tolerant bacterial strains were isolated and identified as *Pediococcus pentosaceus* or *Pediococcus acidilactici*.

A large culture collection containing lactic acid bacteria was stored at −70° C. in a set of square-well microtiter plates (Beckman Coulter Inc, Fullerton, Calif.; Catalog No. 069681), with each well containing a different bacterial strain. The culture collection was screened for 1-butanol tolerant bacteria on an agar medium as follows. The square-well microtiter plates were thawed at 25° C. The Nunc-TSP transferable solid phase screening system (Nalgene Nunc International, Napersville, Ill.; Catalog No. 445497) was used to directly replica-plate the square-well microtiter plates onto Lactobacilli MRS Agar (Acumedia Manufacturers, Lansing, Mich.) containing up to 3.5% (w/v) 1-butanol. The agar contained 0.005% tetrazolium blue chloride to make bacterial growth more visible. Some square-well microtiter plates were subcultured prior to replica plating by inoculating a 50 μL aliquot from each square well into 150 μL of Lactobacilli MRS Broth in the corresponding well of a 96-well "U-bottom" microtiter plate (VWR Scientific Products, West Chester, Pa.; Catalog No. 62409-052). The U-bottom plates were covered with an adhesive cover (Beckman Coulter Inc., Fullerton, Calif.; Catalog No. 538619) and incubated at 37° C. for 4 h. Samples from each U-bottom well were then replica-plated as described above. After 24 h at 37° C., tolerant isolates were identified by growth on MRS agar with 3% or 3.5% (w/v) 1-butanol.

The most tolerant strains were identified by additional testing in MRS broth that contained 0%, 2.5%, or 3% (w/v) 1-butanol. Aliquots of growth medium (150 µL) were dispensed into U-bottom microtiter plates. Each well was inoculated with 25 µL of culture from a different tolerant strain. Bacterial growth in each well was monitored using a Spectra MAX (Molecular Devices Corporation, Sunnyvale, Calif.) to measure the optical density at 600 nm ($OD_{600}$). The microtiter plates were incubated anaerobically at 37° C. for 24 h. All isolates that grew in the presence of 3% (w/v) 1-butanol were collected into two microtiter plates (one strain per well). Additional strains that had the highest levels of growth in 2.5% (w/v) 1-butanol (but did not grow in 3% (w/v) 1-butanol) were also included.

Two butanol tolerant isolates were identified as members of the bacterial genus *Pediococcus* by sequencing the products that resulted from the polymerase chain reaction (PCR) amplification of the 16S rRNA genes that were extracted from the isolates (Table 4). Each isolate was processed using a commercial kit (Ultraclean Microbial Genomic DNA Isolation Kit obtained from Mo Bio Laboratories, Inc, Carlsbad, Calif., Part No. 12224-50). The 16S rRNA genes of the isolates were amplified by PCR using Amplitaq DNA Polymerase (Applied Biosystems, Foster City, Calif., Part No. N808-0166) with primers HK12 (GAGTTTGATCCTGGCT-CAG), given as SEQ ID NO:39, and HK13 (TACCTTGT-TACGACTT), given as SEQ ID NO:40. The PCR conditions were 2 min at 94° C., followed by 30 cycles at 94° C. for 1 min, 55° C. for 1 min, and 72° C. for 1 min, followed by 5 min at 72° C. The PCR products were purified using a commercial kit (Qiagen PCR Purification Kit from Qiagen, Valencia, Calif., Part No. 28104). PCR products were sequenced with four primers, HK12 and HK13, listed above, and JCR14 (ACGGGCGGTGTGTAC) given as SEQ ID NO:41, and JCR15 (GCCAGCAGCCGCGGTA), given as SEQ ID NO:42.

Figure 2:
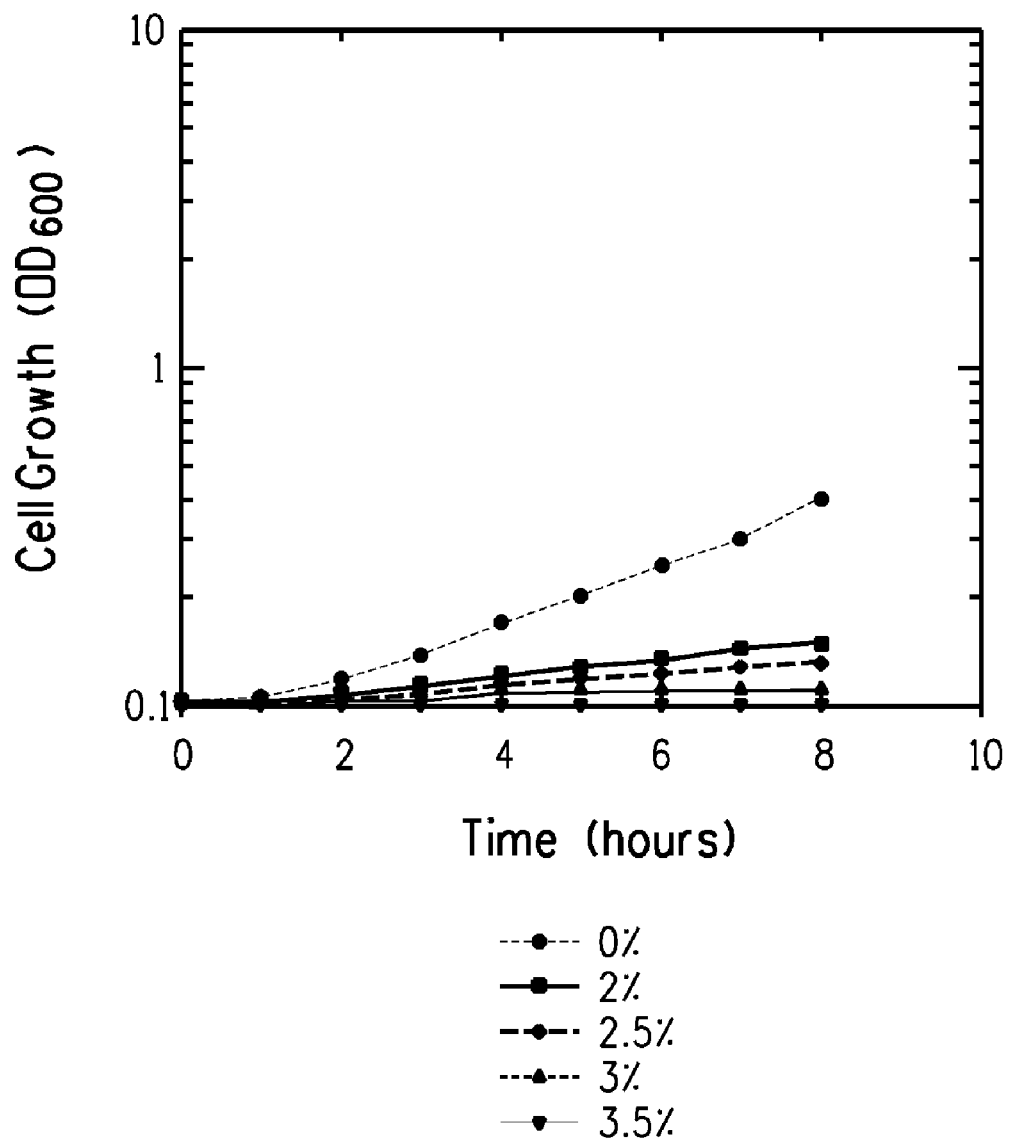
FIG. 2 shows the growth of *Pediococcus acidilactici* strain PN1042 in liquid medium containing 1-butanol at 37° C.

The 1-butanol tolerance of the *Pediococcus* strains was demonstrated in a series of growth experiments conducted with a BioScreen C growth curve instrument (Growth Curves, Ltd., Helsinki, Finland). The isolates were cultured in synthetic liquid growth medium [0.01 M ammonium sulfate, 0.005 M potassium phosphate, pH 7.0, 0.05 M MOPS, pH 7.0 with KOH, 2 mM $MgCl_2$, 0.7 mM $CaCl_2$, 50 µM $MnCl_2$, 1 µM $FeCl_3$, 1 µM $ZnCl_2$, 1.72 µM $CuSO_4$, 2.53 µM $COCl_2$, 2.42 µM $Na_2MoO_4$, 2 µM thiamine hydrochloride, 0.01 M glucose, 0.2% yeast extract (Difco, Detroit, Mich.) and 0.01% casamino acids (Difco, Detroit, Mich.)] at 37° C. in the absence (control flask) and in the presence of various concentrations of 1-butanol (sample flasks, see FIGS. 1 and 2). The growth data was used to calculate the percent growth inhibition caused by 1-butanol by subtracting the percent growth ([$T_0OD_{600}$–$T_5OD_{600}$ for control flask/$T_0OD_{600}$–$T_5OD_{600}$ for sample flask]×100; where $T_0OD_{600}$ is the initial optical density at the starting time and $T_5OD_{600}$ is the optical density after 5 h) from 100%. Growth of strains PN1011 and PN1042 was inhibited 100% by 3.5% (w/v) 1-butanol; however, all both strains displayed low levels of growth in the presence of 3% (w/v) 1-butanol (FIGS. 1 and 2).

TABLE 4

Butanol Tolerant Bacterial Strains
Isolated from a Culture Collection

| Strain | Phylotype | ATCC No. | 16S rRNA Sequence |
|---|---|---|---|
| PN1011 | *Pediococcus pentosaceus* | | SEQ ID NO: 43 |
| PN1042 | *Pediococcus acidilactici* | | SEQ ID NO: 44 |

Example 2

Tolerance of 1-Butanol Tolerant *Pediococcus* to Other Compounds

The purpose of this Example was to test the tolerance of a *Pediococcus* strain isolated based on tolerance to 1-butanol, to the additional compounds isobutanol, 2-butanol and 2-butanone.

The $IC_{50}$ values of PN1011 were determined at 37° C., as follows. The strain was cultured in S30L medium (i.e., 10 mM ammonium sulfate, 5 mM potassium phosphate buffer, pH 7.0, 50 mM MOPS, pH 7.0, 2 mM $MgCl_2$, 0.7 mM $CaCl_2$, 50 µM $MnCl_2$, 1 µM $FeCl_3$, 1 µM $ZnCl_2$, 1.72 µM $CuCl_2$, 2.53 µM $COCl_2$, 2.42 µM $Na_2MoO_4$, 2 µM thiamine hydrochloride, 0.01 M glucose, and 0.2% yeast extract) at 37° C. in the absence (control) and in the presence of various amounts of 1-butanol, isobutanol, 2-butanol or 2-butanone. The doubling time for each culture was calculated from the logarithmic part of the growth curve (doubling time=0.693/growth rate). The percent growth inhibition caused by the butanol compound in the sample flasks was determined by subtracting the percent growth ([doubling time of the control flask/doubling time of the sample flask]×100) from 100%. The $IC_{50}$ was the concentration of butanol that caused 50% growth inhibition and was determined by plotting the concentration of butanol versus percent inhibition. The results are summarized in Table 5.

TABLE 5

Tolerance of PN1011 to 1-butanol, 2-butanol, isobutanol and 2-butanone.

| Compound | $IC_{50}$ (%) |
|---|---|
| 1-butanol | 1.7 |
| isobutanol | 2.2 |
| 2-butanol | 3.0 |
| 2-butanone | 5.4 |

Based on the $IC_{50}$ values determined for each compound and a correlation seen between tolerance to 1-butanol and to each of the other tested compounds, the identified tolerant strains are expected to grow on solid medium containing 4.0% w/v 2-butanol, 3.5% w/v isobutanol, 6.0% w/v 2-butanone.

What is claimed is:

1. A butanol tolerant *Pediococcus* selected from the group consisting of: ATCC:PTA-8068 (*Pediococcus pentosaceus* PN1011), and ATCC:PTA-8069 (*Pediococcus acidilactici* PN1042).

2. A method for the production of butanol comprising:
   a) providing a *Pediococcus* selected from the group consisting of: ATCC:PTA-8068 *Pediococcus pentosaceus* PN1011), and ATCC:PTA-8069 *Pediococcus acidilactici* PN1042), comprising genetic constructs encoding a butanol biosynthetic pathway; and
   b) growing the *Pediococcus* of step (a) under conditions whereby butanol is produced.

3. A method according to claim 2 wherein the butanol is predominantly 1-butanol.

4. A method according to claim 2 wherein the butanol is predominantly 2-butanol.

5. A method according to claim 2 wherein the butanol is predominantly isobutanol.

* * * * *